United States Patent
Takahashi et al.

(10) Patent No.: US 6,347,630 B1
(45) Date of Patent: Feb. 19, 2002

(54) RESPIRATION-SYNCHRONIZED OXYGEN SUPPLYING APPARATUS

(75) Inventors: Masao Takahashi; Masaji Otake, both of Isesaki (JP)

(73) Assignees: Gunma Koike Co., Ltd., Gunma-ken; Koike Medical Co., Inc., Tokyo, both of (JP)

(*) Notice: Subject to any disclaimer, the term of this patent is extended or adjusted under 35 U.S.C. 154(b) by 0 days.

(21) Appl. No.: 09/294,353

(22) Filed: Apr. 20, 1999

(30) Foreign Application Priority Data

Apr. 24, 1998 (JP) .............................. 10-115432

(51) Int. Cl.⁷ .............................................. A61M 16/00
(52) U.S. Cl. ........................... 128/204.21; 128/204.18; 128/204.23; 128/205.24
(58) Field of Search ............... 128/204.23, 204.18, 128/204.24, 205.24, 203.15, 205.12, 204.21

(56) References Cited

U.S. PATENT DOCUMENTS

| | | | |
|---|---|---|---|
| 4,784,130 A | * 11/1988 | Kenyon et al. | 128/204.21 |
| 4,848,332 A | 7/1989 | Champain | |
| 5,058,601 A | * 10/1991 | Riker | 128/725 |
| 5,199,424 A | * 4/1993 | Sullivan et al. | 128/204.18 |
| 5,503,146 A | * 4/1996 | Froehlich et al. | 128/204.23 |
| 5,522,382 A | * 6/1996 | Sullivan et al. | 128/204.23 |
| 5,694,920 A | * 12/1997 | Abrams et al. | 128/200.16 |
| 5,890,490 A | * 4/1999 | Aylsworth et al. | 128/203.12 |
| 6,026,809 A | * 2/2000 | Abrams et al. | 128/203.15 |
| 6,029,660 A | * 2/2000 | Calluaud et al. | 128/203.12 |

FOREIGN PATENT DOCUMENTS

| | | |
|---|---|---|
| EP | 0786265 A | 7/1997 |
| EP | 0903160 A | 3/1999 |
| WO | WO8402080 A | 6/1984 |
| WO | WO9218201 A | 10/1992 |

* cited by examiner

Primary Examiner—John G. Weiss
Assistant Examiner—V. Srivastava
(74) Attorney, Agent, or Firm—Townsend & Banta

(57) ABSTRACT

A respiration-synchronized oxygen supplying apparatus includes a sensor detecting respiration of human being, a valve connecting and disconnecting communications between a first gas passage coupled to the human being and a second gas passage coupled to the oxygen supplier, and a controller for controlling the valve based on information from the sensor. A negative pressure generating mechanism is provided having a communication area widened as closer to the human being between the valve and the human being, and a third gas passage is coupled to the negative pressure generating mechanism to normally communicate between the sensor and the human being. During an oxygen supplying state, oxygen does not leak toward the negative pressure sensor, so that the oxygen can be employed without waste.

2 Claims, 6 Drawing Sheets

(oxygen supplier side) (negative pressure sensor)
(human body side)

(respiration : inhale)

(respiration : exhaust)

RESPIRATION-SYNCHRONIZED OXYGEN SUPPLYING APPARATUS

BACKGROUND OF THE INVENTION

1. Field of the Invention

This invention relates to a respiration-synchronized oxygen supplying apparatus detecting respiration of a human being by means of a sensor thereof and supplying oxygen in synchrony with timings of inhale. More particularly, this invention relates to an oxygen supplying apparatus capable of suppressing oxygen loss down to a lower level with a simple structure without use of a three-way valve.

2. Description of Prior Art

Recently, in a site of medical treatment in a home or in emergency, a combination of an oxygen cylinder and an oxygen supplier easily provides medical treatments which supplies oxygen. Since an oxygen cylinder used for such a purpose is made compact in consideration of portability or the like, it is a concern how to reduce oxygen consumption. For this reason, respiration-synchronized oxygen supply apparatuses which supply oxygen at proper timing in an appropriate amount in synchrony with respiration are now becoming majority.

As such a respiration-synchronized oxygen supplying apparatus, for example, an oxygen supplying apparatus shown in FIG. 6 has been proposed. The oxygen supplying apparatus 51 includes a negative pressure sensor 52, a three-way valve 53 having a first port 53a, a second port 53b, and a third port 53c, and a controller 54 for switching the three-way valve 53 based on information from the negative pressure sensor 52.

A cannula, not shown, is coupled to the first port 53a of the three-way valve 53 and connected to a human being (body of human being) P, while an oxygen cylinder, not shown, is coupled to the second port 53b as for oxygen supplier G. The third port 53c is connected to the negative pressure sensor 52.

In this system, the three-way valve 53 communicates the first and third ports with each other at a standby stage, thereby communicating the human being P and the negative pressure sensor 52 with each other. When the human being makes respiration in this situation, the negative pressure sensor 52 detects inhale of human being and reports it to the controller 54. The controller 54, in response to this, immediately switches the three-way valve 53 as to communicate the first and second ports 53a, 53b with each other, thereby supplying oxygen from the oxygen supplier G to the human being P.

The controller 54, after passing a certain period, makes the three-way valve 53 back to a state that the first and third ports 53a, 53c are in communication with each other, or namely a standby state, and repeats the above control upon detection of inhales of the human being.

According to such a conventional apparatus, supply of oxygen in proper synchrony with inhaling timing in respiration of human being can suppress oxygen consumption of the oxygen supplier G and extend time for use. In addition to this advantageous point, because the three-way valve 53 cuts off the communication between the oxygen supplier G and the negative pressure 52 while oxygen is supplied, the valve can prevent the oxygen to be supplied from escaping toward the negative pressure sensor 52, suppress unnecessary oxygen consumption, allow the user to effectively use the oxygen in a limited amount contained in the compact oxygen cylinder.

It is to be noted that the respiration-synchronized oxygen supplying apparatus described above is specifically disclosed in Japanese Patent Publication (KOKOKU) Heisei 4-3,229.

With the above conventional apparatus, however, there was a problem that the apparatus lacks good durability because the three-way valve switches with high frequency between a state coupling between the first and third ports 53a, 53c (the standby state) and the other state coupling between the first and second ports 53a, 53b (the oxygen supply state).

To solve this problem, a simplified structure in which the negative pressure sensor 52 is made in direct communication with the human being P and which a two-way valve is provided to simply open and close a passage between the oxygen supplier G and the human being P may be conceivable, but with this structure, oxygen normally leaks toward the negative sensor 52 while oxygen is supplied, thereby raising again a fundamental problem that time for use is shortened where the oxygen amount is limited.

SUMMARY OF THE INVENTION

It is an object to provide an oxygen supplying apparatus having an improved durability with a simply structured valve capable of preventing oxygen from leaking toward a negative pressure sensor even while oxygen is supplied.

The foregoing object is accomplished by a respiration-synchronized oxygen supplying apparatus according to the invention which includes a sensor detecting inhale of respiration of a human being; a valve installed between a first gas passage coupled with the human being and a second gas passage coupled with an oxygen supplier; a controller for controlling the valve based on information from the sensor; a negative pressure generating mechanism having a gas communication area that becomes larger as comes closer to the side of the human being from the side the oxygen supplier; and a third gas passage provided with the negative pressure generating mechanism for normally communicating the sensor with the human being.

According to an embodiment of the invention, in a respiration-synchronized oxygen supplying apparatus, the sensor includes a casing having first and second passage holes, and a planer piezoelectric device contained in the casing whose plane faces to the first passage hole and does not face to the second passage hole, where the second passage hole of the sensor is coupled to the third gas passage. With this structure, the oxygen supplying apparatus can possess good durability without receiving loads of positive pressure due to exhale of respiration.

DETAILED DESCRIPTION OF PREFERRED EMBODIMENTS

Figure 1:
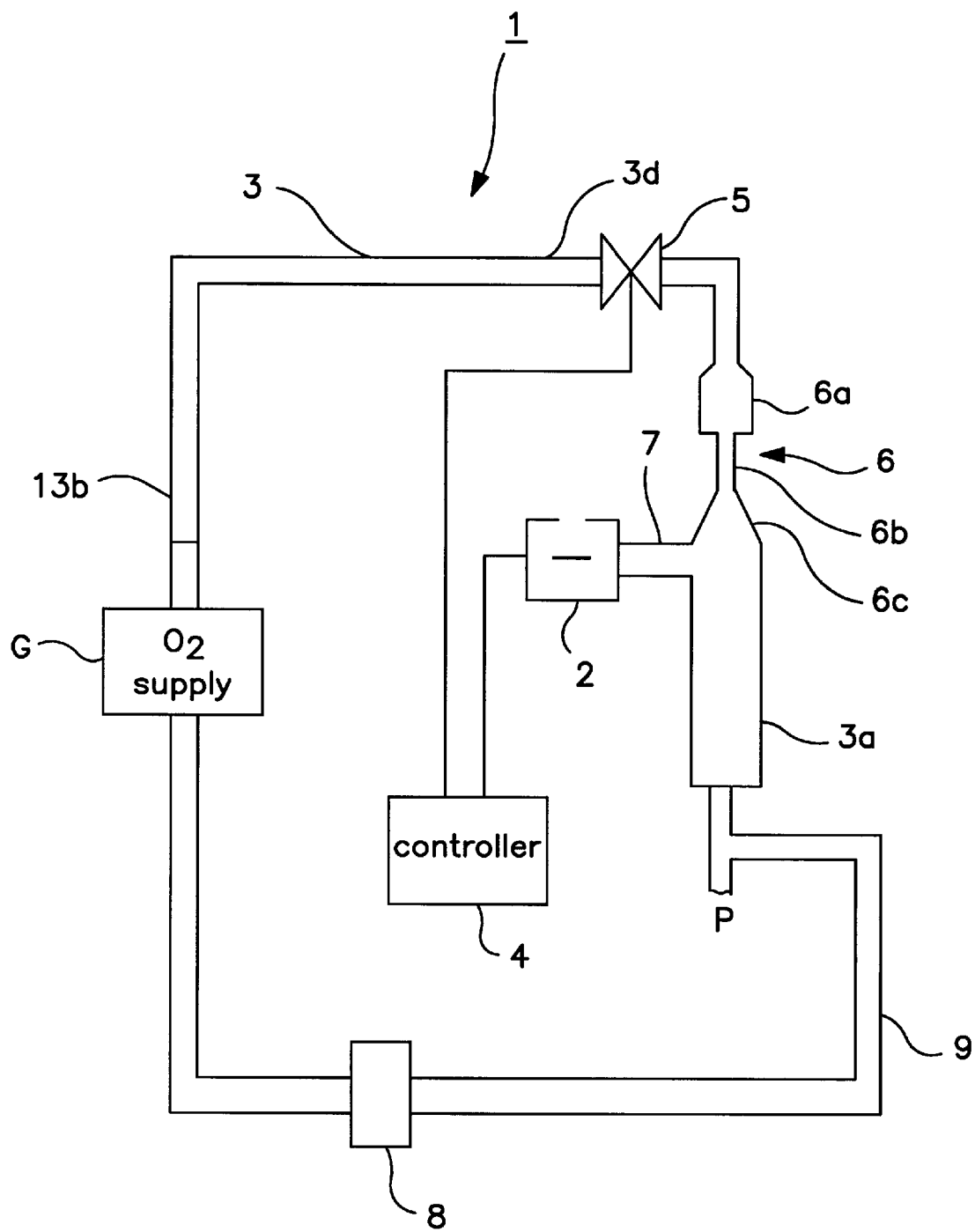
FIG. 1 is a cross section showing an oxygen supplying apparatus according to a first embodiment of the invention.
Figure 2:
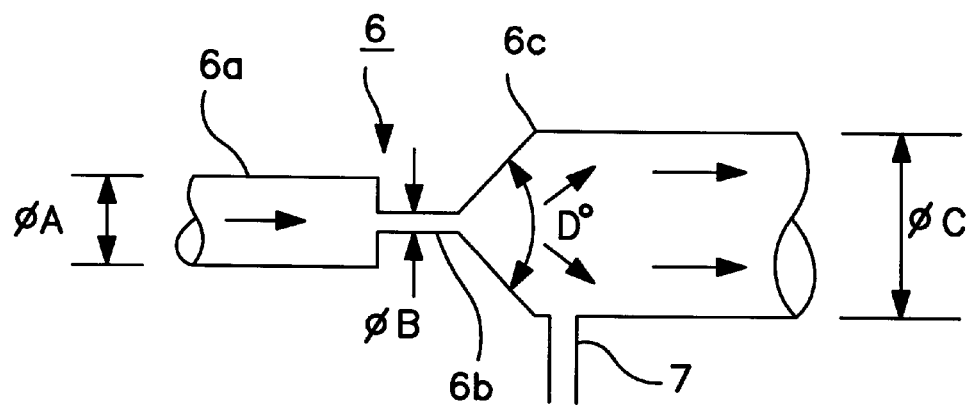
FIG. 2 is a diagram showing a structure of a negative pressure generating mechanism.
Figure 3A:
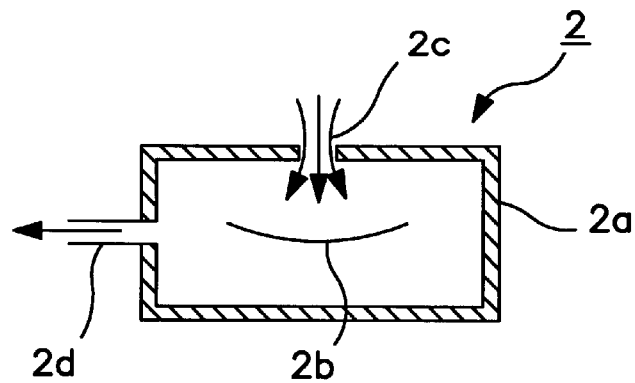
FIGS. 3(*a* & *b*) is an illustration showing operation of the planer piezoelectric sensor.

Referring to FIGS. 1 to 4, a respiration-synchronized oxygen supplying apparatus (hereinafter referred simply to as "oxygen supplying apparatus") according to the first embodiment of the invention is described. FIG. 1 is a cross section showing an oxygen supplying apparatus according to a first embodiment of the invention; FIG. 2 is a diagram showing a structure of a negative pressure generating mechanism; FIG. 3 is an illustration showing operation of the planer piezoelectric sensor; FIG. 4 is an illustration showing operation of the oxygen supplying apparatus. The oxygen supplying apparatus is a portable type that can be used in home or outside and is an apparatus effectuating oxygen supply from a compact oxygen cylinder.

As shown in FIG. 1, the oxygen supplying apparatus according to this embodiment includes a negative pressure sensor 2 having a planer piezoelectric device, a two-way valve 3 having a first port (first gas passage) 3*a*, and a second port (second gas passage) 3*b*, a controller 4, and a mechanical valve 8 for continuously supplying oxygen in an emergency situation. Such an oxygen supplying apparatus is contained in a casing where the first port 3*a* projecting from the casing is coupled to a human being P by way of a cannula not shown as well as the second port 3*b* projecting from the casing is coupled to an oxygen supplier G such as an oxygen cylinder not shown.

A valve body 5 is disposed in a gas passage 3*d* in the two-way valve 3, and two-state operation, connecting and disconnecting states of gas communication between the first and second ports 3*a*, 3*b*, is made by switching the valve 5. A negative pressure generating mechanism 6 is arranged between the first port 3*a* and the valve body 5 at a midway of the gas passage 3*d* in the two-way valve 3.

FIG. 2 shows an enlarged view of the vicinity of the negative pressure generating mechanism. The negative pressure generating mechanism 6 is constituted of an introduction portion 6*a*, an orifice portion 6*b*, and an expanded diameter portion 6*c* when seen from the oxygen supplier side to the human being side. The orifice portion 6*b* has a narrower diameter in comparison with the diameter of the introduction portion 6*a*, and the expanded diameter portion 6*c*, to the contrary, has a wider diameter in comparison with the diameter of the orifice portion 6*b*. The expanded diameter portion 6*c* has a diameter widened in a tapered shape and is connected to a branching gas passage (third gas passage) 7 coupled to the negative pressure sensor 2 and located immediately next to the widened diameter thereof.

That is, where the diameter of the introduction portion 6*a* is $\Phi A$, where the diameter of the orifice portion is $\Phi B$, and where the expanded diameter portion is $\Phi C$, the diameters have conditions of $\Phi B < \Phi A$, and $\Phi B < \Phi C$, but the relation between $\Phi A$ and $\Phi C$ is not restricted. Where the opening angle of the expanded diameter portion 6*c* is D, it is preferable to set D>180.

According to this structure, when oxygen is supplied from the oxygen supplier toward the human being, gas flow rapidly squeezed toward the orifice portion 6*b* from the introduction portion 6*a* is expanded again at the expanded diameter portion 6*c*, so that pressure around the expanded diameter portion 6*c* enters negative or low state, and so that no oxygen flows into the branching gas passage 7.

It is to be noted that some negative pressure may be exerted to the negative pressure sensor 2 by way of the branching gas passage 7 since pressure around the expanded diameter portion 6*c* becomes lower where a large amount of oxygen passes. In this situation, however, the negative pressure is smaller than that at a time of respiration and therefore, the controller 4 can execute a control for detecting whether inhale of respiration or suction while oxygen is supplied by setting a threshold level between respiration and suction.

Now referring to FIG. 3, the structure and operation of the negative pressure sensor 2 is described. As shown in FIG. 3(*a*), the negative pressure sensor 2 is provided with a planer piezoelectric device 2*b* installed in a sealing type casing 2*a* which is in a flat box shape.

The casing 2*a* has a first vent 2*c* located at a position facing the planer surface of the planer piezoelectric device 2*b* and a second vent 2*d* located at a position not facing the planer surface of the planer piezoelectric device 2*b* but facing an edge of the planer piezoelectric device 2*b*. The first vent 2*c* is for gas communication between the interior and exterior of the casing 2*a*, and the second vent 2*d* is coupled with the branching gas passage 7 formed at the negative pressure generating mechanism 6. That is, the negative pressure sensor 2 is normally connected to the human being side P.

In this situation, if a user inhales during his respiration, the gas in the casing 2*a* is discharged from the second vent 2*d*, and to compensate this, external gas flows into the casing 2*a* through the first vent 2*c*. The airflow entered at that time hits the planer piezoelectric device 2*b* which is facing the first vent 2*c*, bending the device to make the apparatus detect the inhale state upon generation of electricity (see, FIG. 3(*a*)).

On the other hand, if the user exhales during his respiration, gas flows into the casing 2*a* from the second vent 2*d*, discharges gas through the first vent 2*c* by a portion of increased pressure in the casing 2*a*. In this situation, however, the air entered from the second vent 2*d* flows in parallel with the flat surface portion of the planer piezoelectric device 2*b*, and the planer piezoelectric device 2*b* does not transform because the airflow does not hit the flat surface portion. Therefore, this negative sensor 2 does not operate during exhale of respiration (see, FIG. 3(*b*)).

As described above, the negative pressure sensor 2 detects only the inhale state of respiration and does not generate any signal during the exhale state. The controller 4 receives signals from the negative pressure sensor 2 and makes control to open the value body 5 in the two-way valve 3 in synchrony with the timing of the signals. After the valve body 5 is opened, after a certain time passes or after oxygen in a certain amount is supplied, a sequence control is executed to close the valve body 5 again.

The mechanical valve 8 is a valve disposed on an auxiliary passage 9 directly coupling to the human being P from the oxygen supplier G. This mechanical valve 8 can continuously supply oxygen through the auxiliary passage 9 by opening the valve 8, if the controller 4 or the valve body 5 is malfunctioned as to stop oxygen supply in use of the normal oxygen supplying way.

Figure 4A:
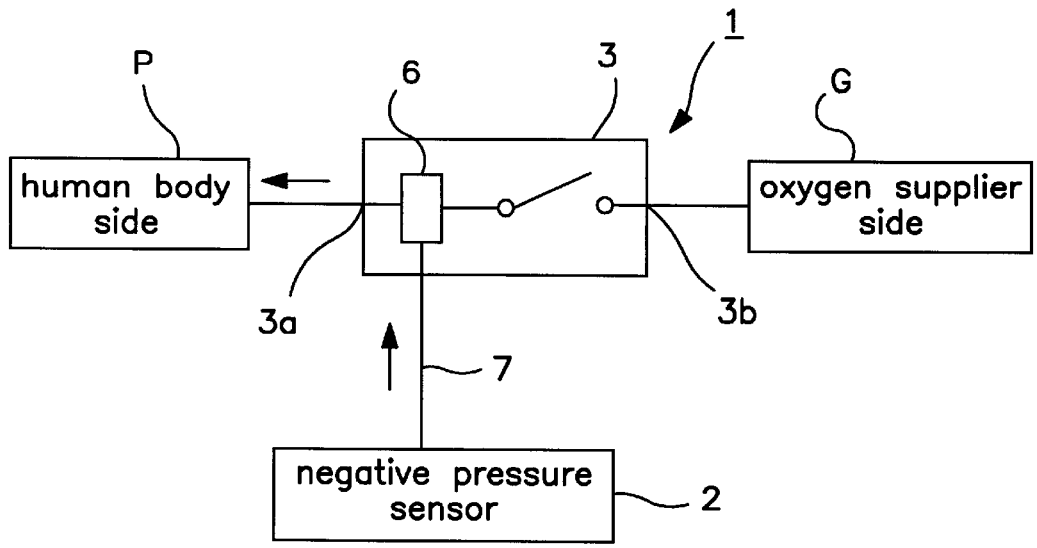
FIGS. 4(*a* & *b*) is an illustration showing operation of the oxygen supplying apparatus.
Figure 4B:
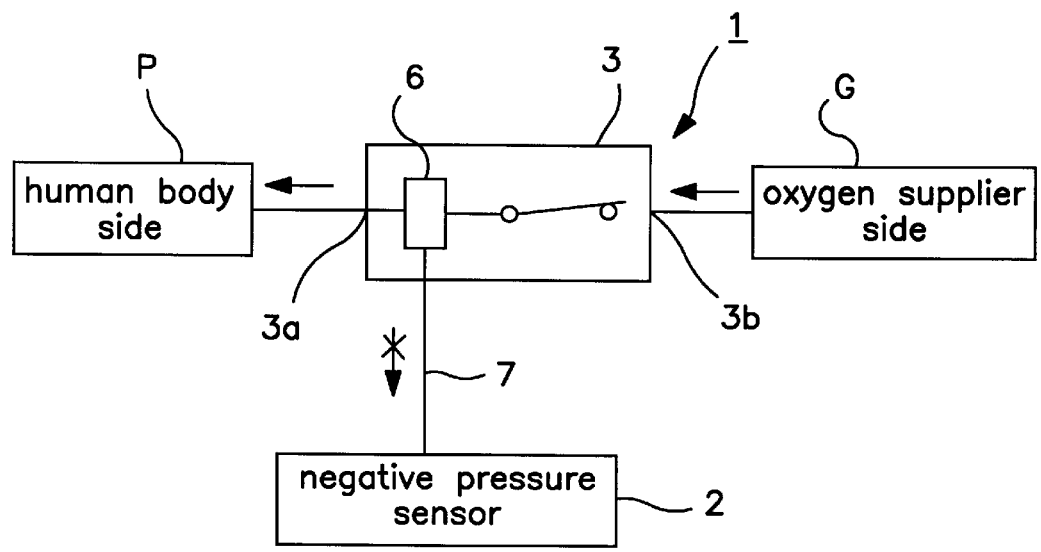

Referring to FIG. 4, operation of the oxygen supplying apparatus of this embodiment is described. FIG. 4(a) is an illustration showing a state that the inhale timing of a user is detected (the standby state) in the oxygen supplying apparatus; FIG. 4(b) is an illustration showing a state that oxygen is supplied from the oxygen supplier to the user (the oxygen supply state.

First, as shown in FIG. 4(a), the first port 3a of the oxygen supplying apparatus 1 is connected to a human being P as the user in this situation using a cannula or mask, while the second port 3b is connected to an oxygen supplier G such as an oxygen cylinder, and thereby preparation work is completed. In this situation, the two-way valve 3 cuts off communication between the first and second ports 3a, 3b and enters in a standby state in which no oxygen is supplied for the human being P.

On the other hand, the human being P is in communication with the negative pressure sensor 2 by way of the negative pressure generating mechanism 6, and when the user inhales during respiration, the above-mentioned negative pressure sensor 2 immediately sense it and transmits signals to the controller 4.

As shown in FIG. 4(b), the controller 4 operates the two-way valve 3 according to the signals from the negative pressure sensor 2, thereby entering to the oxygen supply state in which the first and second ports 3a, 3b are communicated with each other to supply oxygen to the human being P.

At that time, although the oxygen supplier G is in communication with the negative pressure sensor 2, the supplied oxygen does not leak toward the negative pressure sensor 2 by means of the negative pressure generating mechanism 6, and therefore, no oxygen is consumed in a useless manner from the oxygen cylinder.

After oxygen is supplied for a certain time or in a certain amount, the controller 4 operates the two-way valve 3 to disconnect the communication between the first and second ports 3a, 3b again, and returns the apparatus to the standby state. The negative pressure sensor 2, after this, detects the inhale timing during respiration again and repeats the above operation, so that the apparatus can supply oxygen non-continuously in synchrony with the respiration of the user.

Thus, according to the oxygen supplying apparatus 1 of this embodiment, oxygen can be supplied without waste in synchrony with respiration of the user, particularly, the inhale timing, from the oxygen supplier side, and therefore, a portable oxygen cylinder can be used for a longer period. The oxygen supplying apparatus 1 according to this embodiment becomes an apparatus having a high durability because the apparatus 1 has a very simple structure in use of the two-way valve 3 and does fewer movements. In addition, since the negative pressure generating mechanism 6 prevents oxygen from leaking toward the negative pressure sensor 2 in the oxygen supply state, no oxygen is consumed uselessly.

Figure 3B:
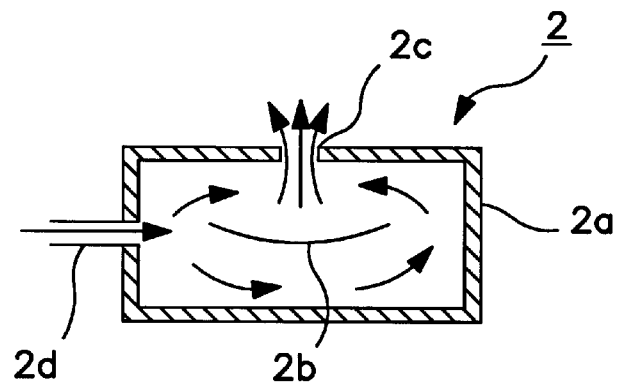

Furthermore, in the standby state, even if the human being makes some exhale, the positive pressure does not become a load to the planer piezoelectric device 2b of the negative pressure sensor 2 (see, FIG. 3(b)), so that the oxygen supplying apparatus 1 has a further excellent durability. The negative pressure sensor 2 does not operate under positive pressure, thereby preventing the controller 4 from malfunctioning.

Figure 5:
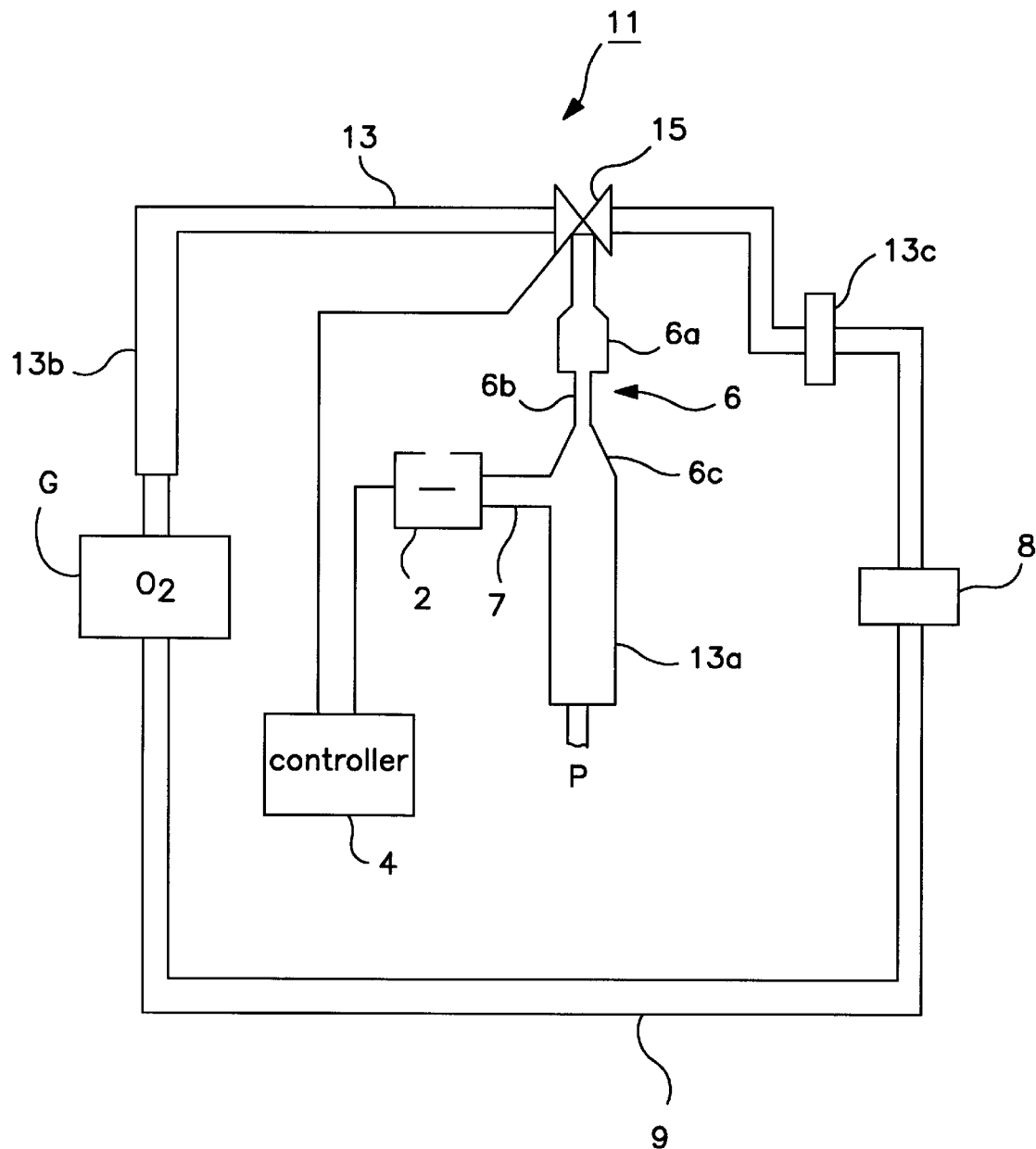
FIG. 5 is a cross section showing an oxygen supplying apparatus according to a second embodiment of the invention.
Figure 6:
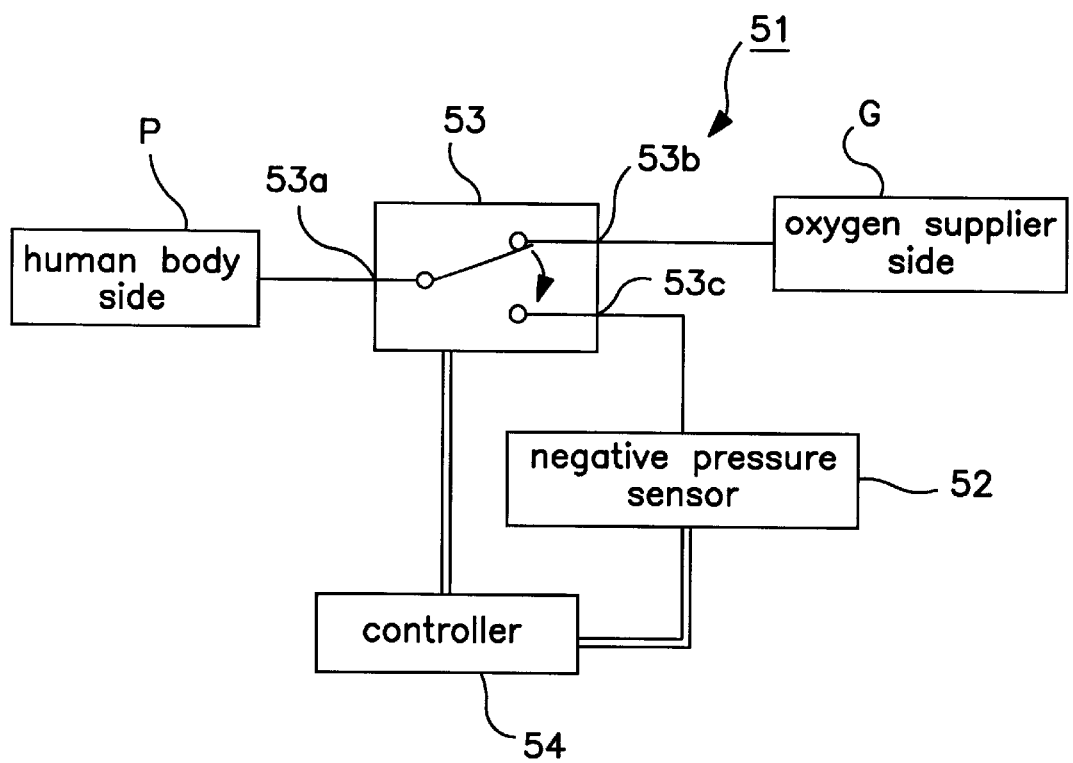
FIG. 6 is a diagram showing a structure of a conventional oxygen supplying apparatus.

Referring to FIG. 5, a second embodiment of the invention is described. FIG. 5 is a cross section showing an oxygen supplying apparatus according to the second embodiment. The oxygen supplying apparatus 11 according to this embodiment has a non-self-holding type three-way valve 13 as a valve, to which an auxiliary passage 9 for a mechanical valve 8 is coupled. The other structure is the same as that of the first embodiment, and the description is omitted upon providing the same reference numbers.

As shown in FIG. 5, incorporated in the oxygen supplying apparatus 11 is the three-way valve 13 having the first, second, and third ports 13a, 13b, 13c. The first and second ports 13a, 13b are coupled to the human being P and the oxygen supplier G, respectively. The third port 13c is coupled to the oxygen supplier G by way of the auxiliary passage 9, and a mechanical valve 8 is installed in a midway.

A valve body 15 disposed at a three-way branching point of the passage 13d in the three way valve 13 selectively communicates between the first port 13a (on a side of the human being P) and the second port 13b (on a side of the oxygen supplier G) and between the first port 13a (on a side of the human being P) and the third port 13c (for the mechanical valve 8). The negative pressure generating mechanism 6 is installed between the valve body 15 and the first port 3a, similarly to the first embodiment.

The valve body 15 is a valve of the non-self-holding type, and communicates between the first and third ports 13a, 13c in a normal situation where it is not controlled by the controller. However, since the mechanical valve 8 mechanically shuts down the third port 13c normally, the three-way valve 13 as a result works in the same manner as the two-way valve in the first embodiment, or namely, make two-state operation, connecting and disconnecting states of gas communication between the first and second ports 13a, 13b.

In case of emergency where the three-way valve becomes uncontrollable from the controller 4 due to, e.g., run out of batteries, the non-self-holding type valve body 15 communicates between the first and third ports 13a, 13c, and therefore, oxygen can be supplied to the human being P through the auxiliary passage 9 only by opening the mechanical valve 8.

Thus, according to the oxygen supplying apparatus 11 of the second embodiment, the auxiliary passage 9 having the mechanical valve 8 can be controlled with the same valve (the three-way valve) as the first and second ports 13a, 13b.

It is to be noted that although the oxygen supplying apparatuses 1, 11 in the first and second embodiments are provided with the negative pressure generating mechanism 6 arranged within the valves 3, 13, such a mechanism can be disposed at any location between the valve body 5, 15 and the human being P, and also, can be provided as a separate apparatus outside the valve 3, 13.

As described above, according to the oxygen supplying apparatus of this invention, the valve repeatedly operates no more than two-state operation of supplying oxygen and not supplying oxygen, basically, and the structure of the valve relating to the oxygen supply can be simplified, so that the oxygen supplying apparatus can be constituted with a good durability.

Moreover, since the third gas passage for the negative pressure sensor is connected to the negative pressure generating mechanism, no oxygen supplied from the oxygen supplier leaks toward the negative pressure sensor, so that oxygen in a limited amount of the oxygen supplier can be used usefully.

Where the oxygen supplying apparatus is formed with the negative pressure sensor having the planer piezoelectric device, the piezoelectric device of the negative pressure sensor is free from load of a positive pressure during exhale of respiration, and the controller can supply oxygen with a proper timing because the positive pressure is not sensed.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention should not be limited by the specification, but defined claims set forth below.

What is claimed is:

1. A respiration-synchronized oxygen supplying apparatus comprising:
    a sensor to detect respiration of a patient, the sensor having a casing with a planar piezoelectric device having a planar face disposed in the casing, a first vent being formed in the casing parallel to the planar face of the piezoelectric element, and a second vent being formed in the casing perpendicular to the planar face of the planar piezoelectric device;
    a valve disposed between a first gas passage, which is adapted to be coupled to a patient and a second gas passage, which is coupled with an oxygen supplier;
    a controller for opening the valve when the sensor detects inhalation of the patient;
    negative pressure generating means disposed between the sensor and the first gas passage having a gas communication area having a first end closer to the patient and a second end farther from the patient, and having a volume which decreases from the second end to the first end; and
    a third gas passage connecting to the negative pressure generating means communicating to the second vent of the sensor.

2. The respiration-synchronized oxygen supplying apparatus according to claim 1, wherein the oxygen supplier is an oxygen cylinder.

* * * * *